United States Patent [19]

Orlando et al.

[11] 4,380,582

[45] Apr. 19, 1983

[54] PREPARATION OF DRY VARIOLA VIRUS

[75] Inventors: Michael D. Orlando; Jean M. Riley, both of Frederick, Md.

[73] Assignee: The United States of America as represented by the Secretary of the Army, Washington, D.C.

[21] Appl. No.: 471,791

[22] Filed: Jul. 9, 1965

[51] Int. Cl.³ ............................................. C12N 5/00
[52] U.S. Cl. .................................. 435/239; 89/1 A; 435/235; 435/260; 435/948
[58] Field of Search ............... 167/78, 78 V, 78.5, 167/54, 39, 82, 46; 252/305; 435/239, 235, 260, 948; 89/1 A

[56] References Cited

U.S. PATENT DOCUMENTS

| | | | |
|---|---|---|---|
| 2,965,544 | 12/1960 | Cabasso | 167/78.5 |
| 3,135,661 | 6/1964 | Bartell et al. | 167/78 |
| 3,186,908 | 6/1965 | Rightsel et al. | 167/78 |
| 3,214,340 | 10/1965 | Laurence | 167/78 |

OTHER PUBLICATIONS

Vaccination of Poultry, 1956, pp. 1-6.
Textbook of Virology 3rd ed., Rhodes et al., Williams & Wilkins Co., 1958, pp. 53-59.

*Primary Examiner*—Stephen J. Lechert, Jr.
*Attorney, Agent, or Firm*—Nathan Edelberg; Robert P. Gibson; Muzio B. Roberto

[57] ABSTRACT

A method of preparing a variola virus which comprises growing the virus on the embryos of chicken eggs, recoverng the inoculated embryos, stabilizing the recovered embryos with a mixture comprising; lactose, raffinose, lysine, sodium glutamate, dextrin, isoniazid and thiourea.

1 Claim, No Drawings

PREPARATION OF DRY VARIOLA VIRUS

The invention described herein may be manufactured and used by or for the Government of the United States of America for governmental purposes without the payment to us of any royalty thereon.

This invention relates to a method of preparing variola virus. More specifically, it relates to a method of growing the virus on the embryo of a chicken egg, separating the embryo, purifying, stabilizing and freeze drying the concentrated virus. The dried product is associated with good biological and aerobiological characteristics and is highly infectious for monkeys.

Specifically, 11 day old embryonated non-disinfected eggs are candled and the eggs containing areas of well-developed chorioallantoic membranes devoid of large blood vessels are selected. Three holes are drilled through the shell (one hole over the center of the air space and two holes over the selected chorioallantoic membrane area). An artificial air space is created by applying a vacuum to the hole drilled over the center of the air space and making a tiny hole in the fibers of the membrane covering the hole over the chorioallantoic area which in turn drops the chorioallantoic membrane. The egg is then rotated so that the chorioallantoic membrane is now directly beneath the second hole.

A secondary seed of a variola virus in the amount of 0.1 milliliter is inoculated on the dropped chorioallantoic membrane utilizing a one milliliter tuberculin syringe. The inoculated eggs are rolled slightly to insure distribution of the inoculum over the exposed chorioallantoic membrane. The unsealed eggs are then placed on their long axis in trays with the dropped chorioallantoic membrane facing upward and incubated at a temperature of around 35° C. for a period of 66 hours.

The infected chorioallantoic membranes are harvested by cutting the egg in half along the long axis and detaching.

The harvested chorioallantoic membranes are treated with a 1% trypsin solution and stirred for 15 minutes at a temperature of around 37° C. An 80% suspension of the chorioallantoic membrane in an aqueous solution is prepared in a stabilizer comprising: 2.5% lactose, 2.5% raffinose, 1.5% lysine, 1.5% sodium glutamate, 1.5% dextrin, 0.5% isoniazid and 0.5% thiourea. The resultant mixture is agitated for a period of 5 minutes and centrifuged lightly (1,000 g), for 3 minutes to remove particulates. The virus in the supernatant is concentrated in a Sharpless centrifuge at 6000 rpms for 30 minutes (52,000 g). The sediment containing the virus is resuspended in the stabilizer in a ratio of 1 gram of the sediment to 10 milliliters of the stabilizer, agitated for a period of five minutes and lightly centrifuged (1,000 g), for 3 minutes. The supernatant containing the virus is frozen as pellets on a modified drum pelleter at a temperature of around −40° C.

The frozen pellets are placed in 15 milliliter vaccine vials and inserted into the platen of a Waffle iron drier at a temperature of −18° C.

The dried material is pooled in a dry cabinent using nitrogen as an inert atmosphere to reduce relative humidity to less than one percent. The pooled, dried material is ground lightly with a mortor and pestle.

The dried material is packaged in approximately one gram samples in 15 milliliter vaccine vials, stoppered under nitrogen, placed in containers with silica gel and stored at a temperature of 70° C.

The seed stock utilized was the Yamada strain of variola virus and titered $1 \times 10^5$ pox infectious units (PIU), per milliliter. Forty 11 day old embryonated eggs were inoculated on the chorioallantoic membrane with a $10^{-1}$ dilution of parent seed. After the eggs were incubated at a temperature of 35° C. for a period of 72 hours, the chorioallantoic membranes were harvested and a suspension thereof was made in heart infusion broth containing 500 units of penicillin and 100 milligrams of streptomycin per milliliter. The suspension was agitated for a period of two minutes, centrifuged (1000 g) for a period of three minutes, distributed into vials in two milliliter amounts and stored at a temperature of −70° C. These vials of variola virus, which are bacteria free, constitute the primary seed stock.

Five hundred, 11 day old embryonated eggs were inoculated on the chorioallantoic membrane with a 0.1 milliliter of a $10^{-3}$ dilution of the primary seed stock. The heart infusion broth used for this dilution contained four milligrams per milliliter of colymycin in addition to the standard amount of penicillin and streptomycin. After incubation at a temperature of 35° C. for a period of 72 hours, the chorioallantoic membrane was harvested and diluted in a ratio of 1:10 by weight with heart infusion broth containing the above mentioned amounts of colymycin, penicillin, streptomycin and in addition polymysin B. The diluted chlorioallantoic membranes are homogenized and centrifuged to remove gross particulates.

The variola virus containing dried final product, when stored at temperatures of 26° and 37° C. had an $AC_{50}$ greater than 42 days. In addition, the dried product was stored for three years at temperatures of −18° and −70° C. with no significant loss in titer.

The physical and biological characteristics associated with the variola virus containing dried final product are summarized below:
(1) virus concentration; PIU/gm $9.83 \times 10^8$
(2) bulk density; 0.418 grams per milliliter
(3) residual moisture; 2.7%
(4) particle size; 14 microns (mass medium diameter)
(5) aerosol characteristics at 75° F.;
  (a) source strength, 11.5%
  (b) decay rate, %/min
    physical: 2.4
    biological: 0.0
    Total: 2.4

The variola virus containing dried final product was subjected to the following test:

EXAMPLE I

The final product was aerosolized in two gram amounts. The relative humidity was held at 50% at a temperature 72° F. The aerosols were sampled using an all glass impinger with British pre-impinger which samples all particles less than 5 microns with: (a) ten milliliters of 10 percent aqueous skim milk solution plus two drops of sterile olive oil and (b) a flow rate of 12.5 liters of air per minute for five minutes. The biological data obtained is summarized in Table I below.

TABLE I

| TITER | Percentage Recovery | | Total Decay | $10^6$ PIU Air Borne | |
|---|---|---|---|---|---|
| $10^8$ PIU/gm | 6 mins | 60 mins | Rate, %/min | 6 mins | 60 mins |
| 0.98 | 4.1 | 0.6 | 2.8 | 4.18 | 0.59 |

EXAMPLE II

The stabilized concentration of chorioallantoic membranes were treated with fluorescin in an amount of one milligram of the fluorescin per milliliter of the stabilized concentrate prior to freeze drying. The variola virus containing dried final product was subsequently treated as described in Example I above. The biological and physical data obtained is summarized in Table II below:

TABLE II

| Titer $10^8$ PIU/gm | BIOLOGICAL | | PHYSICAL | |
|---|---|---|---|---|
| | Extrapolated Source Strength % | Total Decay Rate %/min | Extrapolated Source Strength % | Decay Rate %/min |
| 34.7 | 11.5 | 2.4 | 23.5 | 2.4 |

EXAMPLE III

Fourteen cynomolgus monkeys were exposed to the final products in aerosol form for a period of 4 minutes to determine the respiratory infectivity thereof. The effect of exposure of the monkeys is summarized in Table III below:

TABLE III

| Dose Range PIU | MONKEYS | | |
|---|---|---|---|
| | Exposed | Survivors | Positive Serology |
| 11,000–87,000 | 7 | 7 | 7 |

All of the monkeys demonstrated a severe exanthema of the face, trunk and extremities. The determination of an $lD_{50}$ dose was not attempted in this test. However, it appears from the data that the $lD_{50}$ would be lower than 11,000 PIU. This is a significant improvement over the previously reported aerosol characteristic of dry variola.

We claim:

1. In a process for the preparation of a variola virus which comprises the steps of: chorioallantoic inoculation of the embryos of fertile chicken eggs, incubating the eggs for a period of time sufficient to cultivate the virus, separating the embryos from the rest of the eggs, stabilizing the embryos, homogenizing, differential centrifuging the resultant slurry, freezing the slurry into pellets and drying the pellets under a vacuum; the improvement wherein the stabilizing comprises the addition of: 2.5% lactose, 2.5% raffinose, 1.5% lysine, 1.5% sodium glutamate, 1.5% dextrin, 0.5% isoniazid, and 0.5% thiourea, per volume of embryos.

* * * * *